Figure 1:
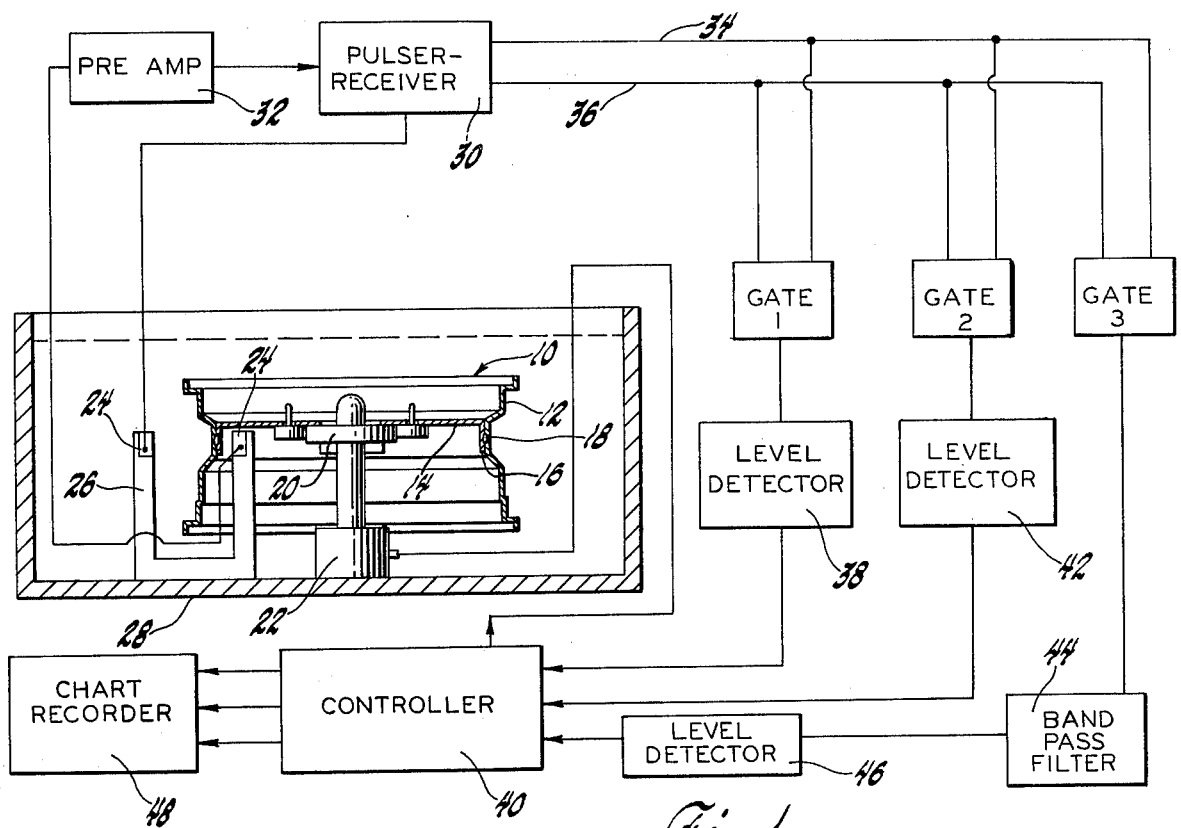

United States Patent [19]

Dubetz et al.

[11] 4,265,119
[45] May 5, 1981

[54] ULTRASONIC METHOD OF INSPECTING SPOT WELDS

[75] Inventors: Martin W. Dubetz, Sterling Heights; Umit Bilge, St. Clair Shores, both of Mich.

[73] Assignee: General Motors Corporation, Detroit, Mich.

[21] Appl. No.: 99,074

[22] Filed: Nov. 30, 1979

[51] Int. Cl.³ .............................................. G01N 29/00
[52] U.S. Cl. ......................................... 73/588; 73/612
[58] Field of Search ................. 73/588, 599, 609, 610, 73/612, 613, 614, 615, 616, 620, 624, 627, 628, 629

[56] References Cited

U.S. PATENT DOCUMENTS

| | | | |
|---|---|---|---|
| 3,554,029 | 1/1971 | Deininger, Jr. | 73/614 |
| 3,791,199 | 2/1974 | Toth et al. | 73/609 |
| 4,158,308 | 6/1979 | Sharpe et al. | 73/609 |

*Primary Examiner*—Stephen A. Kreitman
*Attorney, Agent, or Firm*—Warren D. Hill

[57] ABSTRACT

To obtain a measure of the size of a spot weld nugget, the weld is scanned with an ultrasonic beam of about 20 megahertz frequency. The ultrasonic signal transmitted through the part is analyzed to determine the presence of the part and the presence of a weld. The detected signal is gated to pass a portion of the signal which has been multiply reflected through the weld region to a bandpass filter which passes frequencies that are selectively attenuated by a weld nugget much more than the surface bond or stick zone surrounding the nugget so that the energy content of the filtered signal is used to determine the presence of nugget material at any point during the scan. A chart recorder controlled according to the energy content of the filtered signal produces a characteristic signature for each weld which distinguishes between the extent of the stick zone and the nugget of each weld so that the weld nugget size is readily determined.

3 Claims, 9 Drawing Figures

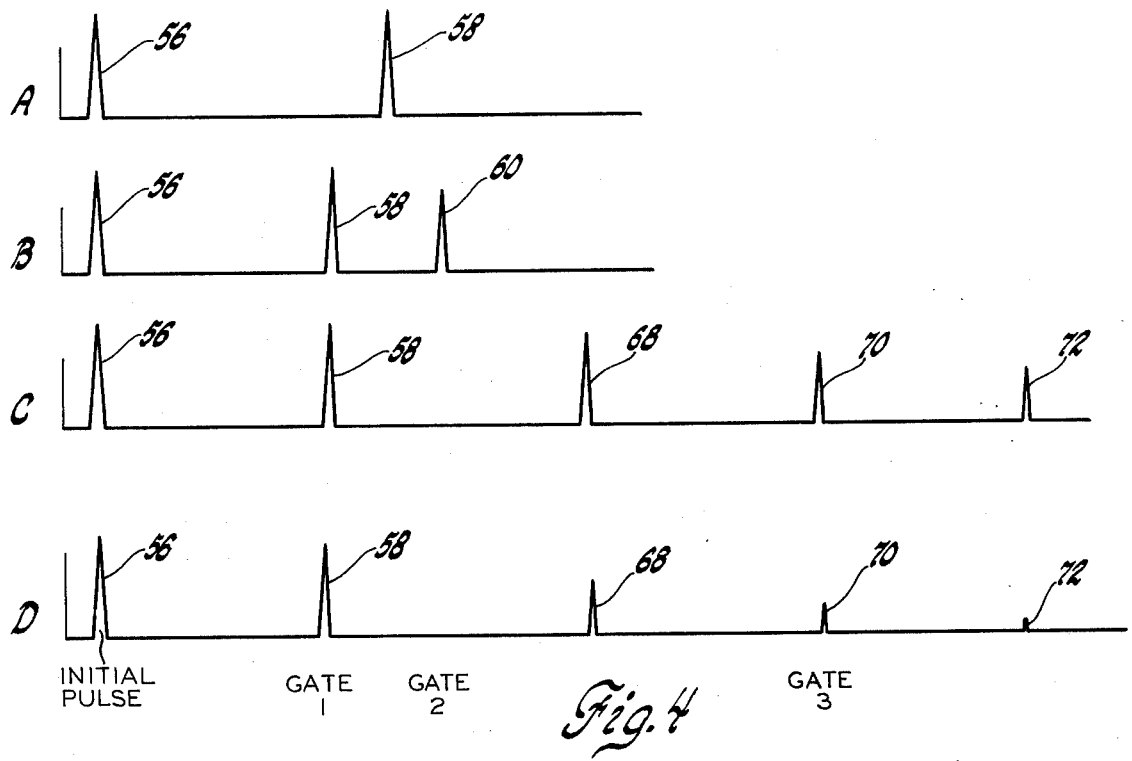
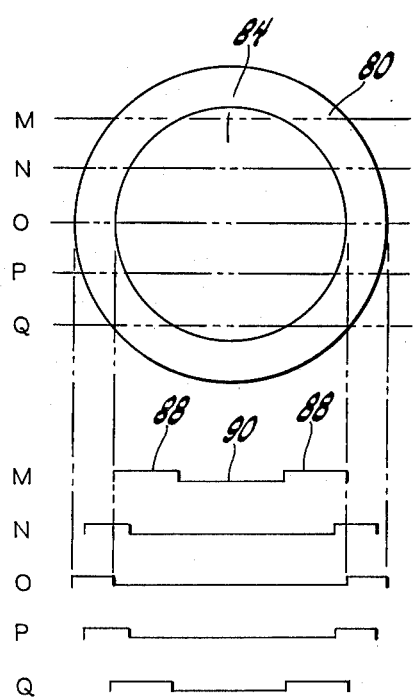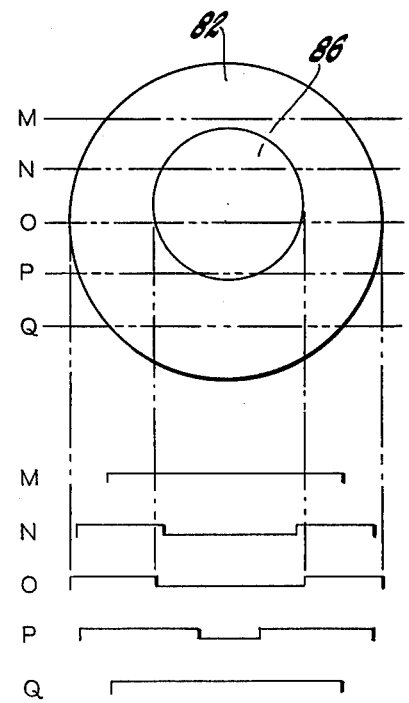

ULTRASONIC METHOD OF INSPECTING SPOT WELDS

This invention relates to a method of measuring weld quality nondestructively and particularly to an ultrasonic spot weld nugget measuring method.

To assure the quality of sheet metal assemblies fabricated by spot welding, it is desirable to obtain a measure of sound nugget material in a weld without destroying the assembly to obtain such a measurement. It is also desirable to make such measurements sufficiently rapidly and inexpensively so that many if not all of the welds made on an article produced in high production quantities can be monitored. Heretofore ultrasonic inspection techniques have been used to determine the presence and the size of welds. Such techniques were based on the phenomenon that if an interface existed between two adjacent parts, an ultrasonic echo would be produced, whereas if the parts were bonded together, the assembly would be sufficiently homogenous in the bond zone that no echo pulse would occur. In practice, however, the bond zone comprises a weld nugget which penetrates deeply into both of the welded parts and frequently includes a stick zone or surface bond surrounding or contiguous with the nugget. Traditional ultrasonic inspection techniques are unable to distinguish between the nugget and the stick zone since in both cases there is no interface between the parts to give rise to an echo pulse. Thus, although a weld zone might be detected it was not known how much of the weld zone is occupied by the nugget as opposed to the stick zone. Consequently, the size of the weld nugget could not be determined.

It is, therefore, a general object of this invention to provide a method for the rapid and inexpensive measurement of weld nugget size in a spot weld. In particular, it is an object of this invention to provide an ultrasonic inspection method for measuring the size of a spot weld nugget.

This invention is carried out by scanning a welded part with an ultrasonic beam having frequencies above about 20 megahertz which includes a band of frequencies which are much more highly attenuated by nugget material than by surrounding material, analyzing the signal transmitted through the part to determine the presence of a weld, detecting a signal which has experienced multiple reflections in the part and filtering the signal to pass the band of frequencies which are highly attenuated by the nugget, determining the amount of energy in the filtered signal for any given scan position to thereby distinguish between a high energy signal correlating to a surface bond region and a low energy signal corresponding to a weld nugget region whereby the extent of the nugget traversed during each scan of the weld is determined.

Figure 2:
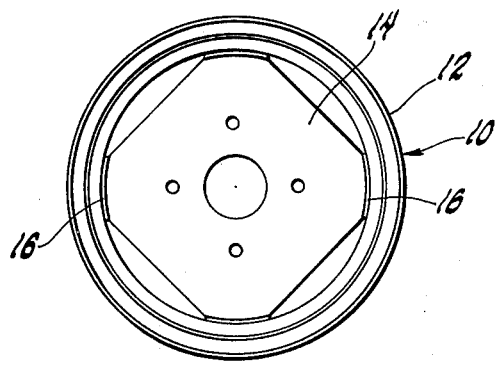
Figure 3:
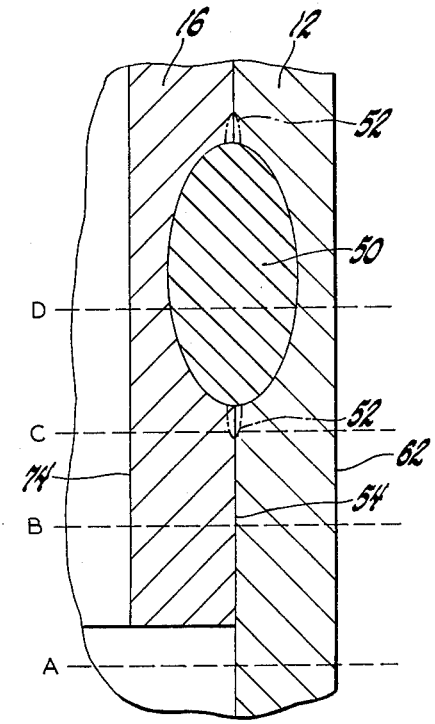

The above and other advantages will be made more apparent from the following specification taken in conjunction with the accompanying drawings wherein like reference numerals refer to like parts and wherein:

FIG. 1 is a schematic diagram of an apparatus and circuit for inspecting welds on an article according to the method of the invention, FIG. 2 is an elevational view of the article being inspected in FIG. 1, FIG. 3 is a cross-sectional view of two parts joined by a weld, FIGS. 4A through 4D are waveforms representing ultrasonic pulses generated by inspection of various sections of the parts of FIG. 3, and FIGS. 5A and 5B respectively are illustrations of a pair of welds being inspected according to the invention and traces representing the inspection results.

For purposes of illustration, the weld inspection method is described as applied to an automotive wheel. As shown in FIGS. 1 and 2 of the drawings, a wheel 10 comprises a rim 12 and a disc 14. The disc has four flanges 16 which engage the rim and are joined thereto by welds 18. There are two welds on each flange. The wheel is mounted horizontally on a turntable 20 supported and driven by a stepper motor 22 for controllably turning the wheel about its axis. A pair of ultrasonic transducers 24 are mounted on the ends of a U-shaped support 26 which straddles the rim and flange bond area so that ultrasonic pulses may be focused through the weld 18 and detected by the other transducer. The entire assembly is immersed in a container 28 of water so that water serves as the coupling medium of the ultrasonic energy as it passes between the transducers and the wheel. Electronic circuitry for producing, detecting and analyzing ultrasonic signals comprises a pulser-receiver 30 connected to one of the transducers 24 to generate ultrasonic pulses. A preamplifier 32 is connected between the other receiving transducer 24 and the pulser-receiver for detecting the received pulses. The outputs of the pulser receiver are a timing pulse on line 34 synchronous with the emitted pulses and the received RF signal on line 36 representing the detected pulses. Each of these signals is fed to three gates identified as gate 1, gate 2 and gate 3 which are selectively adjusted to pass the RF signal at predetermined gate times to subsequent circuitry. The output of gate 1 is connected to a level detector 38 having a binary output connected to a controller 40. The output of gate 2 is connected to a level detector 42 which has a binary output also connected to the controller 40. The output of gate 3 is connected to a bandpass filter 44 which passes a selected portion of the RF signal to a level detector 46 which has its output connected to the controller 40. The controller outputs in turn are connected to a chart recorder 48 and the stepper motor 22.

A M6800 computer manufactured by Motorola, Inc. is an example of a suitable controller 40. All the gates and level detectors can be provided by a KB6000 ultrasonic inspection system manufactured by Krautkramer-Branson which offers a capability for multiplexing several channels each serving a set of transducers. This allows simultaneous multiple readings for purposes described below.

The method which is carried out by the described apparatus is illustrated by reference by FIGS. 3 and 4. FIG. 3 illustrates two adjacent parts 12 and 16 in cross-section joined by a weld. The weld includes a nugget 50 and an area 52 surrounding the nugget referred to as a stick zone where the parts 12 and 16 are superficially joined by a surface bond. At regions beyond the stick zone 52 the plates 12 and 16 are in casual contact so that an interface 54 is present.

FIG. 4 parts A, B, C and D illustrate ultrasonic pulses transmitted through the assembly of FIG. 3 at locations A, B, C and D respectively. In each part of FIG. 4, the first pulse 56 represents the trigger pulse applied on line 34 at the time the emitting transducer is energized. The second pulse 58 occurring on each line represents the first pulse transmitted through the assembly and detected by a receiving transducer. Location A of FIG. 3 is outside the periphery of the flange 16 so that there the path of an ultrasonic pulse includes only the plate 12. The received pulse 58, as shown in FIG. 4 at A, occurs at a time determined by the distance travelled by the pulse through the water and through the steel plate 12 and the velocity of propagation in each medium. Since the ultrasonic energy has a higher velocity in steel than in water, the amount of steel in the path of the beam influences the time the pulse 58 is received. At location B which includes both plates 12 and 16 the pulse 58 will be received in a shorter time as indicated in FIG. 4B. Thus, by gating the gate 1 open at the proper time as shown in FIG. 4, it can be determined by the level detector 38 whether both pieces 12 and 16 are present at a specific area being inspected. A high or logic "1" output signal from the detector 38 is necessary for a weld to be present.

A second pulse 60 occurs in FIG. 4B. This results from a reflection from the interface 54. That is, the pulse transmitted through the assembly is in part reflected from the bottom 62 of the plate 12 and from the interface 54 and back through the bottom to the detecting transducer. By gating gate 2 open at that point, it can be determined whether there is an interface separating the two parts. In FIG. 4B, the pulse 60 occurring in the gate 2 indicates that a weld is not present. A low or logic "0" signal from the detector 42 is necessary for a weld to be present.

In FIGS. 4C and D the waveforms represent ultrasonic pulses occurring at locations C and D respectively of FIG. 3. The pulse 58 does occur within gate 1 to verify that both parts 12 and 16 are present and no pulse occurs within the gate 2 to reveal that there is no interface between the parts therefore establishing that a weld or bond is present. Thereafter, subsequent pulses 68, 70 and 72 occur as a result of multiple reflections of the pulse between the bottom surface 62 of plate 12 and the top surface 74 of plate 16. The pulses successively diminish in amplitude because of the attenuation occurring in the material, the attenuation, of course, being greater for longer path lengths. While the pulse 58 represents one traverse of the pulse through the parts 12 and 16, the pulse 68 represents three traverses; the pulse 70 represents five traverses and so forth. If ultrasonic pulses of the proper frequency are used, the nugget material 50 will attenuate the pulses to a much greater extent than the base metal of the parts 12 and 16. Thus, the pulse amplitude 68, 70 and 72 of FIG. 4D diminishes more rapidly than those of FIG. 4C. By gating open gate 3 at the proper time one of the pulses, say 70, is selected. It is possible to determine whether the pulse has passed through nugget material or simply the stick zone 52 on the basis of the pulse amplitude. As shown in FIG. 1, the pulse passed by the gate 3 is further passed by the bandpass filter 44 of the appropriate frequency band and then submitted to a level detector 46 which determines whether the amplitude of the resulting pulse 70 is above or below some preset threshold. The output of the level detector 46 is presented to controller 40 as an indication of whether nugget material is present at that point.

Practical experience in the weld inspection of wheels has revealed that the ultrasonic frequencies above about 20 MHz result in a significant distinction between a weld nugget and a stick zone. For example, successful weld nugget measurements were made using transducers nominally rated at 25 MHz and monitoring the frequency band from 27 MHz to 32 MHz. On the other hand, at low frequencies, say 10 or 15 MHz, the attenuation difference between nugget material and the stick zone is not sufficient to allow reliable discrimination between the two. The reason the high frequencies are effective to make such a discrimination is believed to be based on the differences in the grain structure in the two regions. The base metal of the parts 12 and 16 have a fine grain structure and although the material in the stick zone has been affected by the heat, there is no substantial difference between that grain structure and that of the base metal when compared to the very large nugget macrostructure. The nugget 50 has a columnar dendritic macrostructure which attenuates the high frequencies much more than the surrounding metal. This difference in attenuation at high frequencies coupled with the sampling of a multiply reflected pulse makes possible the distinction between the nugget material and the stick zone. For a given application, the optimum frequency band for the inspection method can be determined empirically. Similarly the choice of which reflected pulse to sample is determined empirically, balancing the attenuation difference with signal to noise ratio.

FIGS. 5A and 5B represent a pair of welds 80 and 82 having a large nugget 84 and a small nugget 86, respectively which are scanned along five lines M, N, O, P and Q according to the method of the invention. The figures also illustrate the resulting five chart recorder traces bearing the same identification obtained during the scanning of each of those welds. In the apparatus of FIG. 1, the controller 40 periodically actuates the stepper motor 22 to index the turntable to advance the wheel for effecting a scan through the welds and simultaneously controls the chart recorder 48 to advance the chart in synchronism with the wheel movement. Multiple scans through the welds are effected by vertical movement of the transducers to a new position for each scan by means not illustrated or by using a plurality of transducers at different levels to be energized one at a time or simultaneously on separate channels for simultaneous multiple scans. In any event for each scan line the presence of a weld is verified when the requirements of the gate 1 and gate 2 circuits are met, that is, the apparatus senses two thicknesses of metal between the transducers and senses no interface 64. In that event the chart recorder pen is lowered to the paper to make a mark. When the gate 3 circuit determines that there is a high level of energy passing through the filter 44 indicative of the presence of a stick zone, the pen is positioned to a first level and when a low level of energy passes the filter, the pen is positioned to a second level so that for each scan line a bilevel trace is obtained which reveals the presence of a weld and the character of the weld structure. For example, for the scan line M through the weld 80, the high level 88 of the trace indicates two regions of stick zone and the low level 90 of the trace indicates a portion of weld nugget has been traversed. On the other hand, for weld 82, the scan line M results in a trace at the high level only thereby indicating a stick zone only. By combining the five traces, M through Q, a characteristic signature of the weld is obtained and by observation the size of the weld nugget is readily discerned. Of course, rather than use the chart recorder, the size of each nugget can be computed electronically from the data produced by the level detector 46.

It will thus be seen that the method according to this invention provides for nondestructive measurement of weld nugget size by ultrasonic inspection, and that the method is sufficiently fast and inexpensive to be practical for high volume parts inspection.

The embodiments of the invention in which an exclusive property or privilege is claimed are defined as follows:

1. The method of ultrasonically measuring the size of a weld nugget contiguous to a surface bond region comprising the steps of scanning a welded part with repetitive pulses of an ultrasonic beam having frequencies above 20 MHz and detecting the signal transmitted through the part, analyzing the detected signal to determine the presence of a weld and analyzing the detected signal where a weld is present to measure the nugget size by gating the signal to sample a signal portion which results from a plurality of reflections within the part, filtering the signal to pass only a band of frequencies above about 20 MHz, and determining the amount of high frequency energy in the signal portion wherein a high amount of high frequency energy correlates with a surface bond region and a low amount of high frequency energy correlates with a weld nugget region whereby the extent of the nugget traversed during each scan of a weld is determined.

2. The method of ultrasonically measuring the size of a weld nugget contiguous to a surface bond region, the nugget comprising materials which attenuates ultrasonic energy in a certain band of frequencies to a much greater extent than the material comprising the surface bond region, comprising the steps of scanning a welded part with repetitive ultrasonic pulses having frequencies in the said band and detecting the signal transmitted through the part, analyzing the detected signal to determine the presence of a weld and analyzing the detected signal where a weld is present to measure the nugget size by gating the signal to sample a signal portion which results from a plurality of reflections within the part, filtering the signal to pass only the said band of frequencies, and determining the amount of high frequency energy in the filtered signal wherein a high amount of high frequency energy correlates with a surface bond region and a low amount of high frequency energy correlates with a weld nugget region whereby the extent of the nugget traversed during each scan of a weld is determined.

3. The method of ultrasonically measuring the size of a weld nugget contiguous with a surface bond region comprising the steps of scanning a welded part with repetitive ultrasonic pulses having frequencies above 20 MHz and detecting the signal transmitted through the part, analyzing the detected signal to determine the presence of a weld, analyzing the detected signal where a weld is present to measure the nugget size by gating the signal to sample a signal portion which results from a plurality of reflections within the part, filtering the signal to pass only a band of frequencies above about 20 MHz which are highly attenuated by the weld nugget, and determining the amount of high frequency energy in the filtered signal wherein a high amount of high frequency energy correlates with a surface bond region and a low amount of high frequency energy correlates with a weld nugget region, and controlling a chart recorder to effect chart movement synchronously with part scanning, and when the presence of a weld is detected, recording at either of two levels according to the energy content of the filtered signal whereby a signature characteristic of the weld nugget size is generated on the chart.

* * * * *